US010751230B2

(12) United States Patent
Tsujimoto

(10) Patent No.: US 10,751,230 B2
(45) Date of Patent: Aug. 25, 2020

(54) ABSORBENT BODY AND DEVICE FOR PRODUCING SAME

(71) Applicant: ZUIKO CORPORATION, Settu-shi, Osaka (JP)

(72) Inventor: Yoshio Tsujimoto, Settu (JP)

(73) Assignee: ZUIKO CORPORATION, Settu-Shi, Osaka (JP)

( * ) Notice: Subject to any disclaimer, the term of this patent is extended or adjusted under 35 U.S.C. 154(b) by 694 days.

(21) Appl. No.: 15/033,445

(22) PCT Filed: Oct. 30, 2014

(86) PCT No.: PCT/JP2014/078981
§ 371 (c)(1),
(2) Date: Apr. 29, 2016

(87) PCT Pub. No.: WO2015/072347
PCT Pub. Date: May 21, 2015

(65) Prior Publication Data
US 2016/0250083 A1    Sep. 1, 2016

(30) Foreign Application Priority Data

Nov. 14, 2013  (JP) ................................. 2013-235862

(51) Int. Cl.
*A61F 13/15*  (2006.01)
*A61F 13/20*  (2006.01)
(Continued)

(52) U.S. Cl.
CPC ...... *A61F 13/515* (2013.01); *A61F 13/15634* (2013.01); *A61F 13/15658* (2013.01);
(Continued)

(58) Field of Classification Search
CPC ................ A61F 13/53; A61F 13/53409; A61F 13/53418; A61F 13/515; A61F 13/5323; A61F 13/15658; A61F 13/15634
See application file for complete search history.

(56) References Cited

U.S. PATENT DOCUMENTS 3,733,238 A    5/1973  Long et al.
3,927,673 A *  12/1975  Taylor ................. A61F 13/5323
604/366
(Continued)

FOREIGN PATENT DOCUMENTS

FR    2163743 A1    7/1973
JP    2008-99865 A   5/2008
(Continued)

OTHER PUBLICATIONS

PCT International Search Report of PCT/JP2014/078981.
Europe Patent Office, "Search Report for European Patent Application No. 14861681.6," dated May 12, 2017.

*Primary Examiner* — Michele M Kidwell
(74) *Attorney, Agent, or Firm* — Manabu Kanesaka

(57) ABSTRACT

An absorbent body forming satisfactory connections while webs are conveyed at a high speed includes at least two sheets of nonwoven fabric overlapping each other; connections at which the nonwoven fabric sheets are connected together; and an absorbent material disposed between the nonwoven fabric sheets at a small region encircled by the connections. When seen in a direction perpendicular to a main surface of the nonwoven fabric sheets, a plurality of the connections is formed with spaces therebetween on each side of imaginary polygons compartmentalizing the nonwoven fabric sheets and neighboring each other, and the connection is formed at least on a middle part of the sides common to the imaginary polygons neighboring each other. The connections are formed sequentially, and simultane-
(Continued)

ously arranged in a row parallel to each other, and the minimum number of connections per row is at least 45% of the maximum number of connections per row.

9 Claims, 14 Drawing Sheets

(51) Int. Cl.

| | |
|---|---|
| *A61F 13/515* | (2006.01) |
| *A61F 13/532* | (2006.01) |
| *B29C 65/00* | (2006.01) |
| *B29C 65/78* | (2006.01) |
| *B29C 65/08* | (2006.01) |
| *B32B 38/06* | (2006.01) |
| *A61F 13/53* | (2006.01) |
| *B29C 65/18* | (2006.01) |
| *B32B 37/00* | (2006.01) |
| *B29C 43/24* | (2006.01) |
| *B29K 105/00* | (2006.01) |
| *B29L 7/00* | (2006.01) |
| *B29L 31/48* | (2006.01) |

(52) U.S. Cl.
CPC .. *A61F 13/15723* (2013.01); *A61F 13/15739* (2013.01); *A61F 13/5323* (2013.01); *B29C 65/086* (2013.01); *B29C 65/7847* (2013.01); *B29C 66/1122* (2013.01); *B29C 66/21* (2013.01); *B29C 66/232* (2013.01); *B29C 66/234* (2013.01); *B29C 66/433* (2013.01); *B29C 66/7294* (2013.01); *B29C 66/81433* (2013.01); *B29C 66/83411* (2013.01); *B29C 66/83415* (2013.01); *B32B 38/06* (2013.01); *A61F 2013/15869* (2013.01); *A61F 2013/15878* (2013.01); *A61F 2013/530562* (2013.01); *B29C 43/24* (2013.01); *B29C 65/08* (2013.01); *B29C 65/18* (2013.01); *B29C 66/436* (2013.01); *B29C 66/45* (2013.01); *B29C 66/83413* (2013.01); *B29C 66/849* (2013.01); *B29K 2105/256* (2013.01); *B29L 2007/00* (2013.01); *B29L 2031/4878* (2013.01); *B32B 37/0084* (2013.01); *B32B 2555/02* (2013.01)

(56) References Cited

U.S. PATENT DOCUMENTS

| | | | | |
|---|---|---|---|---|
| 4,360,021 | A * | 11/1982 | Stima | A61F 13/5323 604/365 |
| 5,030,314 | A * | 7/1991 | Lang | A61F 13/15634 156/390 |
| 5,788,684 | A * | 8/1998 | Abuto | A61F 13/532 604/358 |
| 5,900,305 | A | 5/1999 | Chapman | |
| 5,938,650 | A * | 8/1999 | Baer | A61F 13/5323 604/368 |
| 5,994,614 | A | 11/1999 | Wada et al. | |
| 7,524,449 | B2 * | 4/2009 | Walsh | A61F 13/15634 156/62.2 |
| 9,066,835 | B2 * | 6/2015 | Okawa | A61F 13/535 |
| 10,369,246 | B2 * | 8/2019 | Patel | A61F 13/535 |
| 2002/0022427 | A1 | 2/2002 | Curro et al. | |
| 2002/0095127 | A1 * | 7/2002 | Fish | A61F 13/5323 604/368 |
| 2006/0021695 | A1 * | 2/2006 | Blessing | A61F 13/15658 156/196 |
| 2006/0048880 | A1 * | 3/2006 | Blessing | A61F 13/15658 156/60 |
| 2007/0246147 | A1 * | 10/2007 | Venturino | A61F 13/15626 156/73.1 |
| 2009/0187155 | A1 * | 7/2009 | Razavi | A61L 15/46 604/367 |
| 2013/0025795 | A1 | 1/2013 | Ukegawa et al. | |
| 2013/0284361 | A1 | 10/2013 | Tsujimoto et al. | |
| 2013/0284362 | A1 | 10/2013 | Tsujimoto et al. | |

FOREIGN PATENT DOCUMENTS

| | | |
|---|---|---|
| JP | 2009-131510 A | 6/2009 |
| JP | 2012-179220 A | 9/2012 |
| WO | 2012/118235 A1 | 9/2012 |

* cited by examiner

ABSORBENT BODY AND DEVICE FOR PRODUCING SAME

RELATED APPLICATIONS

The present application is National Phase of International Application No. PCT/JP2014/078981 filed Oct. 30, 2014, and claims priority from Japanese Application No. 2013-235862, filed Nov. 14, 2013.

TECHNICAL FIELD

The present invention relates to an absorbent body and a device for producing the same, and particularly relates to an absorbent body provided in a disposable wearing article or the like and a device for producing the same.

BACKGROUND ART

A disposable wearing article such as disposable diapers or trousers and sanitary items for women contains an absorbent body for absorbing a body fluid.

For example, in an absorbent body 200 schematically shown in a main part plan view of FIG. 15, an absorbent material 3 is disposed between overlaid nonwoven fabric sheets and then connections L for connecting together the nonwoven fabric sheets are intermittently formed. The absorbent material 3 is disposed in a manner of being subdivided for each small region encircled by the connections L. As shown in an explanation diagram of FIG. 16, the connections L are formed such that the portion 7 where the absorbent material 3 is inserted and overlaid between webs 1 and 2 composed of continuous sheets of nonwoven fabric is conveyed along the outer peripheral surface of a rotating drum 4 and then the webs 1 and 2 in the overlaid portion 7 are connected together by using an ultrasonic horn 8 (refer to Patent Document 1, for example).

PRIOR ART REFERENCES

Patent Documents

Patent Document 1: International Patent Publication 2012/108331

SUMMARY OF THE INVENTION

Problem to be Solved by the Invention

For example, in FIG. 15, in a case that the webs are conveyed in the right or left direction and then an ultrasonic horn or a heat sealing roll extending in a direction at right angles to the conveyance direction (in the up and down directions in FIG. 15) is pressed against the webs so that the connections L arranged in a direction at right angles to the conveyance direction are formed simultaneously, when a force of pressing the ultrasonic horn or the heat sealing roll against the webs is fixed, an increase and a decrease in the number of connections to be simultaneously formed are repeated in association with the conveyance of the webs and hence variation is caused in the magnitude of the pressure acting on one connection each.

When the pressure acting on the connection is excessively small, connection cannot be established or, alternatively, is easily disengaged even if connection is once established. When the pressure acting on the connection is excessively large, in some cases, the nonwoven fabric is broken at the connection or, alternatively, the connection becomes hard so that the flexibility of the absorbent body is lost. In order that satisfactory connections may be formed, the pressure acting on the connection need be adjusted such as to fall within an appropriate range.

In order that an increase or decrease in the number of connections may be treated, usually, a reaction force obtained at the time of pressing is fed back and then the magnitude of the force (a web-pressing force) of pressing the ultrasonic horn or the heat sealing roll against the webs is changed so that control is performed such that the pressure acting on the connection may fall within an appropriate range.

Nevertheless, when the webs are conveyed at a high speed for the purpose of improvement in the production rate, the period of changing the web-pressing force in accordance with the passage of the connections becomes short. Thus, in a case that the range of fluctuation of the web-pressing force is large, feedback control at a high speed is not easy to be achieved. As a result, it is difficult that satisfactory connections are formed in a state that the webs are conveyed at a high speed.

In view of such situations, the present invention is intended to provide an absorbent body and an absorbent body producing device capable of forming satisfactory connections in a state that webs are conveyed at a high speed.

Means for Solving the Problem

In order to solve the above-described problem, the present invention provides an absorbent body constructed as follows.

An absorbent body includes: (a) at least two sheets of nonwoven fabric overlaid with each other; (b) connections for connecting together the nonwoven fabric sheets; and (c) an absorbent material that is disposed in a small region encircled by the connections between the nonwoven fabric sheets. As for the connections, when viewed in a direction perpendicular to a main surface of the nonwoven fabric sheet, a plurality of the connections are formed with spaces therebetween on each of sides of imaginary polygons that compartmentalize the nonwoven fabric and that are adjacent to each other, and the connections is arranged at least on a middle part of the side common to the imaginary polygons adjacent to each other. The connections are formed sequentially, the connections formed simultaneously are arranged in a row, a plurality of the rows of the connections formed at different times are parallel to each other, and a minimum number of the connections per one of the rows is equal to or greater than 45%, and preferably 50%, of a maximum number of the connections per one of the rows.

According to the above-described configuration, at the time that the connections are formed simultaneously for each row by ultrasonic jointing or heat sealing, even when variation in the magnitude of the pressure acting on each connection is caused in association with fluctuation in the number of connections in each row, the maximum of the pressure acting on the connection can be suppressed, for example, within a range of twice or the like of the minimum. As a result, feedback control at a high speed can stably be performed and hence the pressure acting on each connection can be made within an appropriate range so that satisfactory connections can be formed. Accordingly, satisfactory connections can be formed in a state that the webs are conveyed at a high speed.

Preferably, at least three connections described above are formed on each of the sides of the imaginary polygon.

In this case, the small region in which the absorbent material is disposed can be made larger.

Preferably, all interior angles of the imaginary polygon are 90 degrees or larger.

In this case, the absorbent material can be disposed even to the edges of the small region. By virtue of this, the amount of absorbent material disposed in the small region can be increased so that the absorbability of the absorbent body can be improved.

Preferably, when viewed in the direction perpendicular to the main surface of the nonwoven fabric sheets, the connection has an acute portion protruding parallel to or substantially parallel to a direction in which the side of the imaginary polygon extends.

In this case, the distance between adjacent connections becomes smaller than in a case that the connection has no acute portion. Thus, the absorbent material becomes difficult to pass through between adjacent connections. As a result, the uneven distribution of the absorbent material can be avoided. On the other hand, when the absorbent material swells, the connection between the nonwoven fabric sheets is easily disengaged in the acute portion. Thus, the absorbent material swells to an extent of a case that the connection has no acute portion, or more. As a result, the absorbability of the absorbent body can be maintained or improved. Here, the term "substantially parallel" indicates that the deviation from the parallel is 30° or smaller, preferably 15° or smaller, and more preferably 10° or smaller.

Preferably, as for a pair of end regions, each of which contains the small regions encircled by the connections and which is adjacent to an outer periphery of the nonwoven fabric sheet on each of both sides in a direction at right angles to the rows of the connections, and a middle region which contains the small regions between the pair of end regions, the absorbent material is not disposed in the small region contained in the end region, or an amount of the absorbent material disposed in the small region contained in the end region is substantially smaller than an amount of the absorbent material disposed in the small region contained in the middle region.

In this case, in the small region contained in the end region of the nonwoven fabric sheet, the absorbent material is completely not disposed or is disposed merely in a small amount. When the absorbent body is successively produced by employing webs of nonwoven fabric sheets, the portion where the absorbent material is not disposed can stably be cut. Further, a situation can be avoided that at the time of cutting, the cutter hits the absorbent material so as to be worn out or damaged at an early stage.

Further, the small region where the absorbent material is completely not disposed or is disposed merely in a small amount is arranged adjacent to the outer periphery of the nonwoven fabric sheets on both sides in a direction at right angles to the row of the connections. Thus, a situation can be avoided that the absorbent material disposed in the small region contained in the middle region falls to the outside from the outer periphery of the nonwoven fabric on both sides in a direction at right angles to the row of the connections.

Preferably, the absorbent body further includes plural rows of outer peripheral connections which, when viewed in the direction perpendicular to the main surface of the nonwoven fabric sheet, are arranged with spaces therebetween in the vicinity of an outer periphery of the nonwoven fabric sheet along the outer periphery of the nonwoven fabric sheet and which are adjacent to each other in a direction perpendicular to the outer periphery of the nonwoven fabric sheet. When viewed in a direction perpendicular to the outer periphery of the nonwoven fabric sheet and parallel to the main surface of the nonwoven fabric sheet, the outer peripheral connections in the plural rows overlap with each other as if they were continuous.

In this case, even when the absorbent material disposed in the small region falls to the outside of the small region, the movement is prevented by the outer peripheral connections. Thus, falling to the outside of the outer periphery of the nonwoven fabric sheet can be prevented.

In a particular mode, the shape of the nonwoven fabric sheet may be a square. Instead, a rectangle having a pair of long sides and a pair of short sides may be employed. In the latter case, the connections may be arranged in rows parallel to the pair of short sides. Then, the connections arranged in rows in a direction parallel to the short sides may be formed simultaneously for each row so that the rectangular absorbent body may be produced.

Further, the connections may form in rows parallel to the pair of long sides. In this case, the connections arranged in rows parallel to the long sides may be formed simultaneously for each row so that the rectangular absorbent body may be produced.

Further, for the purpose of resolving the above-described problem, the present invention provides an absorbent body producing device constructed as follows.

An absorbent body producing device includes: (a) a rotating roll having an outer peripheral surface in which protrusions are formed; and (b) an opposing member arranged adjacent to the rotating roll and facing the outer peripheral surface of the rotating roll so as to supply ultrasonic vibration or heat. In the absorbent body producing device, when a first and a second web being at least two sheets of nonwoven fabric pass through between the opposing member and the rotating roll in a state that the first and the second web are overlaid with each other and that an absorbent material is inserted between the first and the second web, with the opposing member urging the webs toward the protrusions, the opposing member supplies the ultrasonic vibration or heat to the webs so that connections at which the webs are connected together are formed in correspondence to the protrusions. As for the protrusions: a plurality of the protrusions are formed with spaces therebetween on each of sides of imaginary polygons that compartmentalize the outer peripheral surface of the rotating roll and that are adjacent to each other; protrusions is formed at least on a middle part of the side common to the imaginary polygons adjacent to each other; and the protrusions are arranged in a plurality of rows parallel to a rotational center axis of the rotating roll, and a minimum number of the protrusions per one of the row is equal to or greater than 45%, and preferably 50%, of a maximum number of the protrusions per one of the row.

According to the above-described configuration, the connections can be formed simultaneously for each row of the protrusions by ultrasonic jointing or heat sealing in which ultrasonic vibration or heat is transmitted from the opposing member to the webs. Even when variation in the magnitude of the pressure acting on each of the simultaneously formed connections is caused in association with fluctuation in the number of protrusions in each row, the maximum of the pressure acting on the connection can be suppressed, for example, within a range of twice or the like of the minimum. As a result, feedback control at a high speed can stably be performed and hence the pressure acting on each connection can be made within an appropriate range so that satisfactory connections can be formed. Accordingly, satisfactory connections can be formed in a state that the webs are conveyed at a high speed.

Preferably, at least three connections described above are formed on each of the sides of the imaginary polygon.

In this case, the small region containing the absorbent body can be made larger.

Preferably, within the outer peripheral surface of the rotating roll, in a mesh-like portion containing the side of the imaginary polygon and extending in a mesh-like shape along the side, the protrusions are formed that protrude from the mesh-like portion to an outer side in a radial direction of the rotating roll. Further, within the outer peripheral surface of the rotating roll, in an inner portion surrounded by the mesh-like portion, a recess is formed that retreats to an inner side in the radial direction of the rotating roll relative to the mesh-like portion.

In this case, at least any one of the first and the second web is arranged along the outer peripheral surface of the rotating roll and then moved together with the outer peripheral surface of the rotating roll in association with rotation of the rotating roll. At that time, the web is deformed along the recess of the rotating roll and then the absorbent material is disposed therein. By virtue of this, the amount of absorbent material disposed in the small region encircled by the connections can be increased so that the absorbability of the absorbent body produced by the absorbent body producing device can be improved.

Preferably, all interior angles of the imaginary polygon are 90 degrees or larger.

In this case, the absorbent material disposed between the webs overlaid with each other can be disposed even to the edges of the small region encircled by the connections. By virtue of this, the amount of absorbent material disposed in the small region can be increased so that the absorbability of the absorbent body produced by the absorbent body producing device can be improved.

Preferably, the protrusion has an acute portion protruding in a direction in which the side of the imaginary polygon extends.

In this case, the distance between adjacent connections becomes smaller than in a case that the connection has no acute portion. Thus, the absorbent material becomes difficult to pass through between adjacent connections. As a result, the uneven distribution of the absorbent material can be avoided. On the other hand, when the absorbent material swells, the connection between the nonwoven fabric sheets is easily disengaged in the acute portion. Thus, the absorbent material swells to an extent of a case that the connection has no acute portion, or more. As a result, the absorbability of the absorbent body produced by the absorbent body producing device can be maintained or improved.

Preferably, the absorbent body producing device further includes plural rows of outer peripheral protrusions that are formed on one side or both sides of the outer peripheral surface of the rotating roll in a direction parallel to the rotational center axis of the rotating roll relative to a region where the protrusions, and that are arranged with spaces therebetween in the plurality of rows in a circumferential direction of the outer peripheral surface of the rotating roll so as to be adjacent to each other in a direction parallel to the rotational center axis of the rotating roll. When viewed in a direction parallel to the rotational center axis, the rows of outer peripheral protrusions overlap with each other as if they were continuous.

In this case, even when the absorbent material disposed in the small region encircled by the connections falls to the outside of the small region, movement of the absorbent body having fallen out is prevented by the outer peripheral protrusions at the portion where the webs are connected together. Thus, a situation can be avoided that the absorbent material falls to the outside of the absorbent body.

Preferably, in a case that at least any one of the first and the second web is arranged along the outer peripheral surface of the rotating roll and moves together with the outer peripheral surface of the rotating roll in association with rotation of the rotating roll, the absorbent body producing device further includes an absorbent material supply unit arranged adjacent to the rotating roll and opposite to the outer peripheral surface of the rotating roll. The absorbent material supply unit supplies the absorbent material to at least one of the first and the second web that are arranged along the outer peripheral surface of the rotating roll and move together with the outer peripheral surface of the rotating roll in association with rotation of the rotating roll, in a manner that supply of the absorbent material is suspended with a fixed period for a portion facing at least three rows of the imaginary polygons arranged in the direction parallel to the rotational center axis of the rotating roll.

In this case, the webs can stably be cut at the portion where the absorbent material is completely not disposed or is disposed merely in a small amount. For example, when the center of the portion where the absorbent material is not disposed is cut, the absorbent material is completely not disposed or is disposed merely in a small amount in one row of small regions adjacent to each of both sides of the cutting portion among the small regions encircled by the connections. Thus, the webs can stably be cut. Further, a situation can be avoided that at the time of cutting, the cutter hits the absorbent material so as to be worn out or damaged at an early stage. Furthermore, a situation can be avoided that the absorbent material disposed in the small regions contained in the middle region except for the end region falls from the cutting portion to the outside.

Effect of the Invention

In an absorbent body and an absorbent body producing device of the present invention, satisfactory connections can be formed in a state that the webs are conveyed at a high speed.

MODE FOR CARRYING OUT THE INVENTION

Hereinafter, embodiments of the present invention will be described below with reference to FIGS. 1 to 14.

Embodiment 1

An absorbent body 10 according to Embodiment 1 of the present invention is described below with reference to FIGS. 1 to 4.

Figure 1:
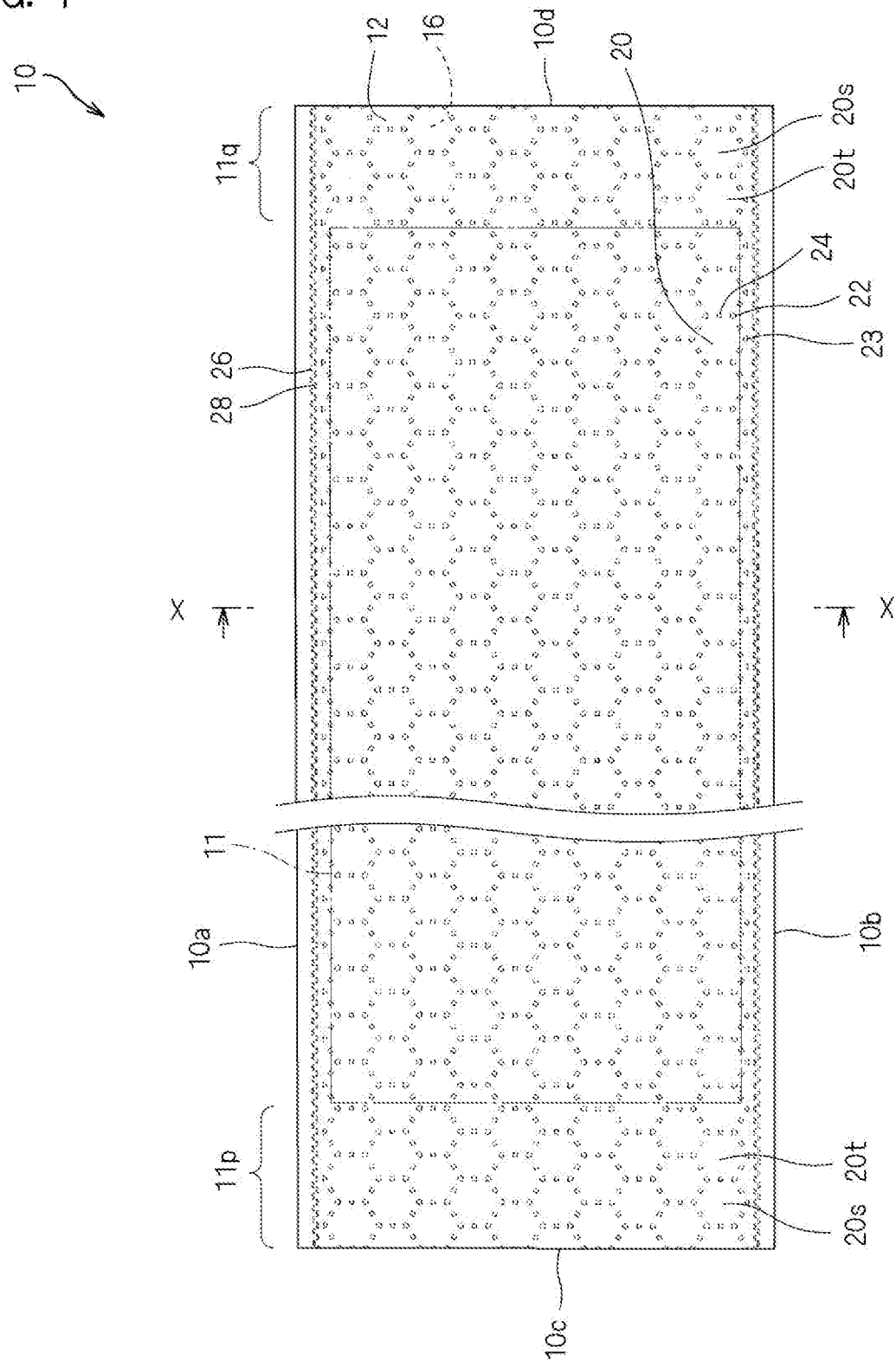
FIG. 1 is a plan view of an absorbent body (Embodiment 1).
Figure 2:
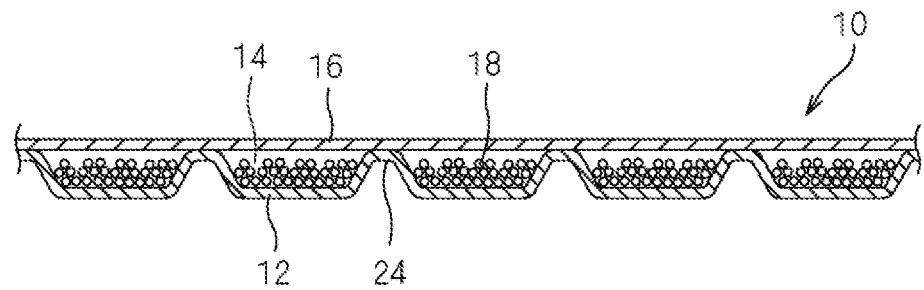
FIG. 2 is a sectional view of an absorbent body (Embodiment 1).

FIG. 1 is a plan view of the absorbent body 10. FIG. 2 is a sectional view of the absorbent body 10 taken along line X-X in FIG. 1.

As shown in FIGS. 1 and 2, in the absorbent body 10, two nonwoven fabric sheets 12 and 16 having a rectangular shape formed by a pair of long sides 10a and 10b as well as a pair of short sides 10c and 10d are overlapping each other, and then connections 22, 23, and 24 are formed for connecting the nonwoven fabric sheets 12 and 16 to each other. In the one nonwoven fabric sheet 12, as shown in FIG. 2, a containing part 14 is formed in each small region 20 encircled by the connections 22, 23, and 24. The containing part 14 contains an absorbent material 18 such as Super Absorbent Polymer (SAP) of granular shape or fibrous pulp having a water absorbing property. The nonwoven fabric sheets 12 and 16 each may be composed of a single sheet of nonwoven fabric or, alternatively, composed of overlaid two or more sheets.

As shown in FIG. 1, the connections 22, 23, and 24 are formed at intervals between the pair of short sides 10c and 10d. Among the small regions 20 each encircled by the connections 22, 23, and 24, the absorbent material 18 is disposed in the small regions 20 overlapping with a middle region 11 indicated by a chain line. On the other hand, in both end regions 11p and 11q adjacent to the short sides 10c and 10d on both sides of the middle region 11, the absorbent material 18 is completely not disposed or is disposed merely in a small amount in at least two rows of small regions 20s and 20t arranged in a zigzag manner between the pair of long sides 10a and 10b.

In a case that the absorbent body 10 is successively produced by using webs each composed of a continuous sheet of nonwoven fabric which is continuous in the longitudinal direction parallel to the long sides 10a and 10b, since the absorbent material 18 is completely not disposed or is disposed merely in a small amount in the vicinity of the short sides 10c and 10d to be cut, the webs can stably be cut without influence from the absorbent material 18. Further, a situation can be avoided that at the time of cutting, the cutter hits the absorbent material so as to be worn out or damaged early. Furthermore, the absorbent material 18 disposed in the small region 20 overlapping with the middle region 11 does not reach the short sides 10c and 10d unless the absorbent material 18 passes through at least two rows of the small regions 20s and 20t where the absorbent material 18 is not disposed in the end regions 11p and 11q. That is, at least the two rows of the small regions 20s and 20t where the absorbent material 18 is completely not disposed or is disposed merely in a small amount in the end regions 11p and 11q avoids a situation that the absorbent material 18 having fallen out from the small regions 20 falls from the short sides 10c and 10d to the outside.

Figure 3:
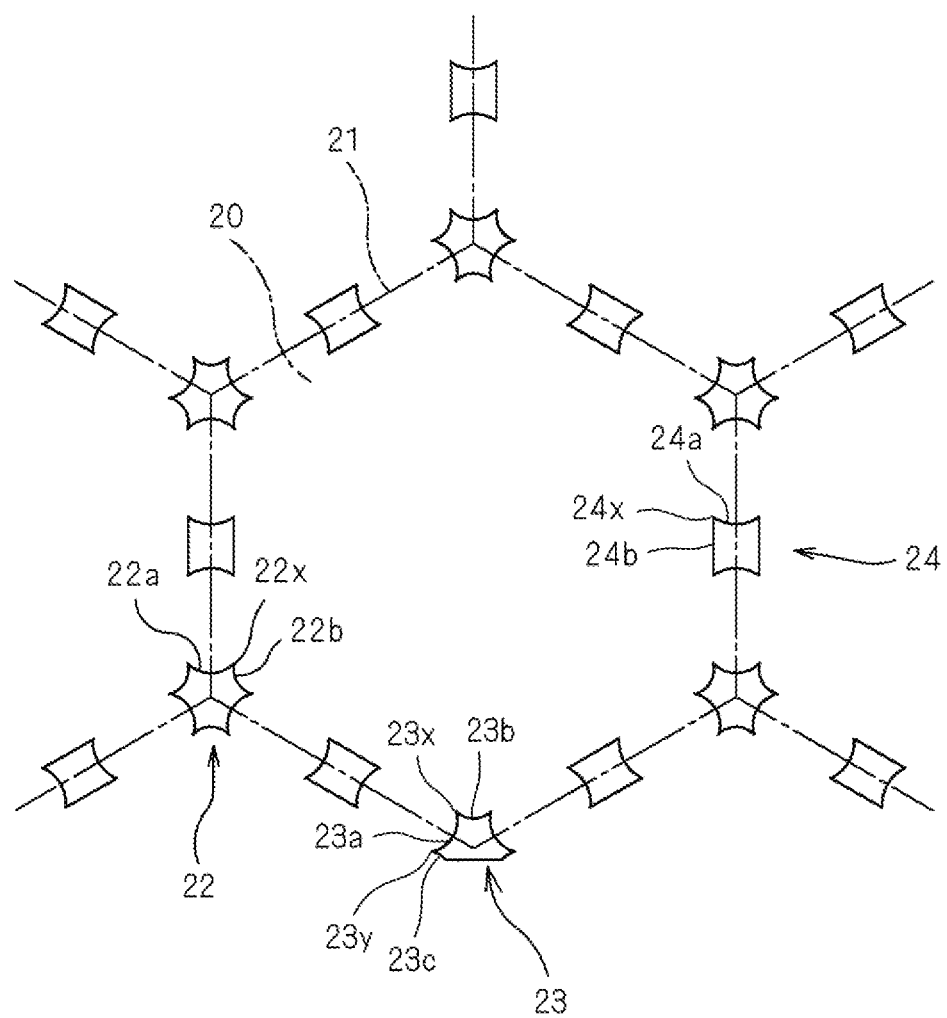
FIG. 3 is a main part enlarged plan view of an absorbent body (Embodiment 1).

FIG. 3 is a main part enlarged plan view of the absorbent body 10. As shown in FIG. 3, when viewed in a direction perpendicular the main surface of the nonwoven fabric sheets 12 and 16, three connections 22, 23, and 24 are formed with spaces therebetween on each side, including on the middle part of the side, of the imaginary polygon 21 for compartmentalizing the nonwoven fabric sheets 12 and 16.

Specifically, the connections 22 and 23 are arranged on corners of the imaginary polygon 21 and have acute portions 22x, 23x, and 23y. The connection 24 is arranged on the middle part within a side of the imaginary polygon 21 and has an acute portion 24x. These acute portions 22x, 23x, 23y, and 24x protrude parallel or substantially parallel to a direction in which a side of the imaginary polygon 21 extends. Here, the term "substantially parallel" indicates that the deviation from the parallel is 30 on 21 extends. Here, the term "substantially e short sides 10c and 10d to t The gap between the adjacent connections 22 and 24 or 23 and 24 is reduced by the acute portions 22x, 23x, 23y, and 24x in comparison with a case of absence of the acute portions 22x, 23x, 23y, and 24x. Thus, the absorbent material 18 becomes difficult to pass through the gap between the adjacent connections 22 and 24 or 23 and 24. On the other hand, when the absorbent material 18 swells, connection of the acute portions 22x, 23x, 23y, and 24x is easily disengaged. Thus, the absorbent material 18 can swell to an extent of a case of absence of the acute portions 22x, 23x, 23y, and 24x, or more. Accordingly, the absorbability of the absorbent body 10 becomes equivalent to that of a case of absence of the acute portions 22x, 23x, 23y, and 24x, or more.

Here, the number of connections formed on each side of the imaginary polygon may be two, three, or more. In the present Embodiment 1, on the side common to the imaginary polygons adjacent to each other, connections are formed on both ends and on the middle part of each side. However, in the present invention, a configuration may be employed that all connections are arranged on the middle parts of the sides of the imaginary polygons and hence no connection is arranged on the corners of the imaginary polygons. In this case, a plurality of connections are arranged on each side of the imaginary polygon.

It is preferable that the connections are arranged at equal intervals. However, employable configurations are not limited to this.

Employable shapes of the connection are not limited to that employed in Embodiment 1. The sides 22a, 22b; 23a, 23b, 23c; and 24a, 24b of the connections 22, 23, and 24 may be curved or straight. The central portions of the connections 22, 23, and 24, except for both ends of the sides 22a, 23a, and 24a intersecting with the sides of the imaginary polygon 21, may have an acute portion that protrudes parallel or substantially parallel to a direction in which the side of the imaginary polygon 21 extends and that reduces the interval between adjacent connections. The connection may have a shape not provided with an acute portion.

The shapes of the imaginary polygons may be suitably selected. Imaginary polygons having plural kinds of shapes may be employed in combination so as to compartmentalize the nonwoven fabric sheets.

The connections 22, 23, and 24 are formed sequentially in a direction parallel to the long sides 10a and 10b by using an absorbent body producing device of Embodiment 2 described later. The connections 22, 23, and 24 arranged in a row parallel to a direction at right angles to the long sides 10a and 10b (a direction parallel to the short sides) are formed simultaneously.

Figure 4:
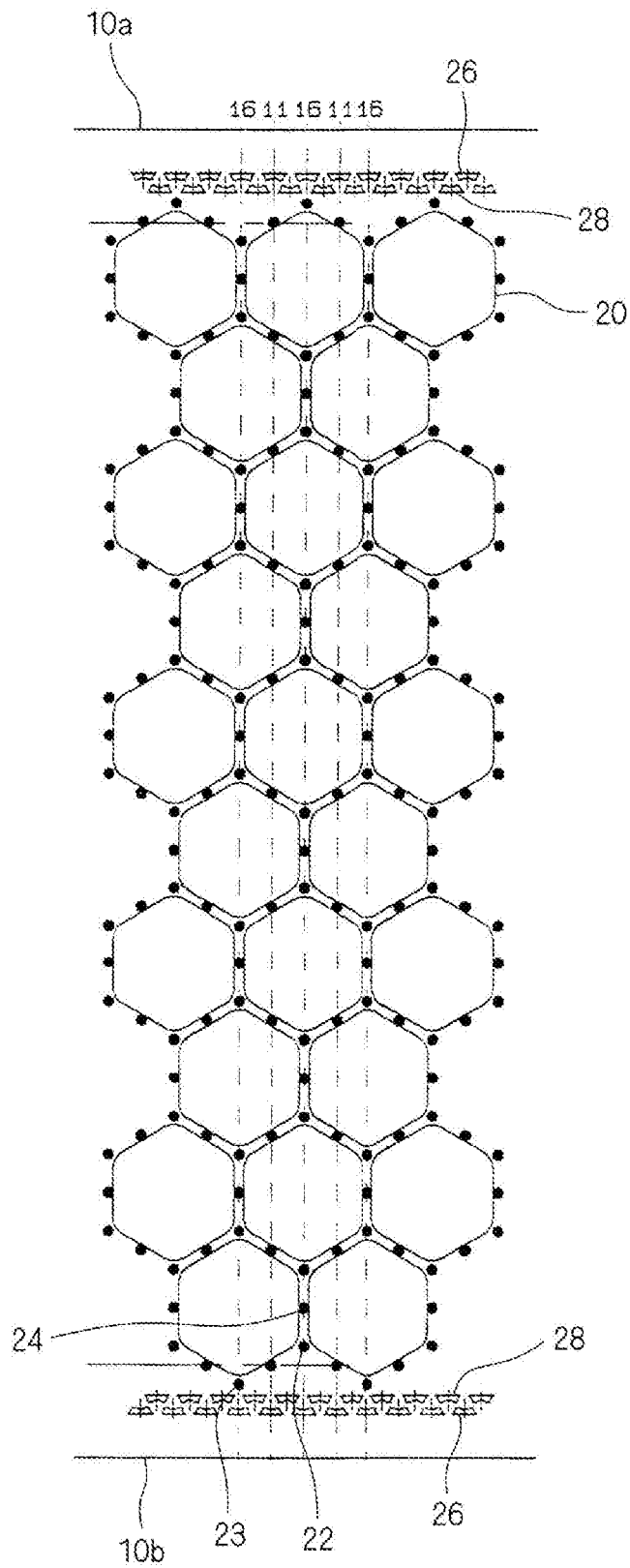
FIG. 4 is a main part plan view of an absorbent body (Embodiment 1).

FIG. 4 is a main part plan view of the absorbent body 10. In FIG. 4, each connection is schematically indicated by a geometrical figure of filled circle "●". The number of connections arranged in a direction parallel to the short sides (in the up and down directions in the figure) is indicated in the vicinity of the long side 10a.

As shown in FIG. 4, the small regions 20 having a regular hexagonal shape encircled by the connections are arranged in the form of a honeycomb, and the small regions 20 are arranged in rows in a direction parallel to the long sides 10a and 10b. Three connections are arranged on each side of the imaginary polygon corresponding to the small region 20.

The connections are arranged in a plurality of rows parallel to a direction at right angles to the long sides 10a and 10b (in a direction parallel to the short sides). As for the number of connections per each of these rows, the minimum number is 11, the maximum number is 16, and hence the minimum number is 69% of the maximum number.

The absorbent body 10 may be produced in such a manner that in a state that the webs of the nonwoven fabric sheets 12 and 16 are moved in a direction parallel to the long sides 10a and 10b, the connections 22, 23, and 24 are formed simultaneously for each row arranged in a direction parallel to the short sides 10c and 10d by ultrasonic jointing or heat sealing and, after that, the webs are cut out.

In this case, even when variation in the magnitude of the pressure acting on each of the connections 22, 23, and 24 is caused in association with fluctuation in the number of the simultaneously formed connections 22, 23, and 24, the maximum of the pressure acting on each of the connection 22, 23, or 24 can be suppressed within a range of twice or the like of the minimum thereof. When the maximum of the pressure acting on the connection can be suppressed within a range of twice or the like of the minimum thereof, feedback control at a high speed can stably be performed and hence satisfactory connections can be formed.

Thus, satisfactory connections can be formed in a state that the webs are conveyed at a high speed (e.g., a conveyance speed of 150 m/min or higher; more specifically, a conveyance speed of 400 m/min).

Further, as shown in FIGS. 1 and 4, two rows of outer peripheral connections 26 and 28 for connecting the nonwoven fabric sheets 12 and 16 to each other are formed in the vicinity of the pair of long sides 10a and 10b, respectively. The outer peripheral connections 26 and 28 may be formed together with the connections 22, 23, and 24 or, alternatively, separately from the connections 22, 23, and 24.

The outer peripheral connections 26 and 28 are individually formed at predetermined intervals along the long sides 10a and 10b. The outer peripheral connections 26 in one row and the outer peripheral connections 28 in the other row are alternately formed with a deviated pitch in a direction parallel to the long sides 10a and 10b. When viewed in a direction perpendicular to the long sides 10a and 10b, the gap between the outer peripheral connections 26 in the one row is covered by the outer peripheral connections 28 in the other row. Thus, when viewed in a direction perpendicular to the outer periphery of the nonwoven fabric sheets and parallel to the main surface of the nonwoven fabric sheets, the outer peripheral connections 26 and 28 in the plural rows overlap with each other as if they were continuous. The outer peripheral connections 26 and 28 are formed in a substantial trapezoid shape. The outer peripheral connections 26 in the outer row are arranged such that the base of the substantial trapezoid shape is located on the outer side. The outer peripheral connections 28 in the inner row are arranged such that the base of the substantial trapezoid shape is located on the inner side. Note that, as for the shapes of the outer peripheral connections 26 and 28, for example, the outer peripheral connections 26 in the outer row and the outer peripheral connections 28 in the inner row may be exchanged with each other. Alternatively, other shapes such as a rectangle may be employed. Even when the absorbent material disposed in the small region 20 falls to the outside of the small region 20, the outer peripheral connections 26 and 28 avoids a situation that the absorbent material falls from the long sides 10a and 10b to the outside. That is, even when the absorbent material disposed in the small region 20 moves to the outer side of the small region 20, the movement of the absorbent material is prevented by the outer peripheral connections 26 and 28.

Modifications 1 to 6 of Embodiment 1 and Comparison Example 1 are described below with reference to FIGS. 5 to 11. In FIGS. 5 to 11, similarly to FIG. 4, each connection is schematically indicated by a geometrical figure of filled circle "●". The number of connections arranged in a direction parallel to the short sides (in the up and down directions in the figure) is indicated in the vicinity of the long side 10a.

<Modification 1>

Figure 5:
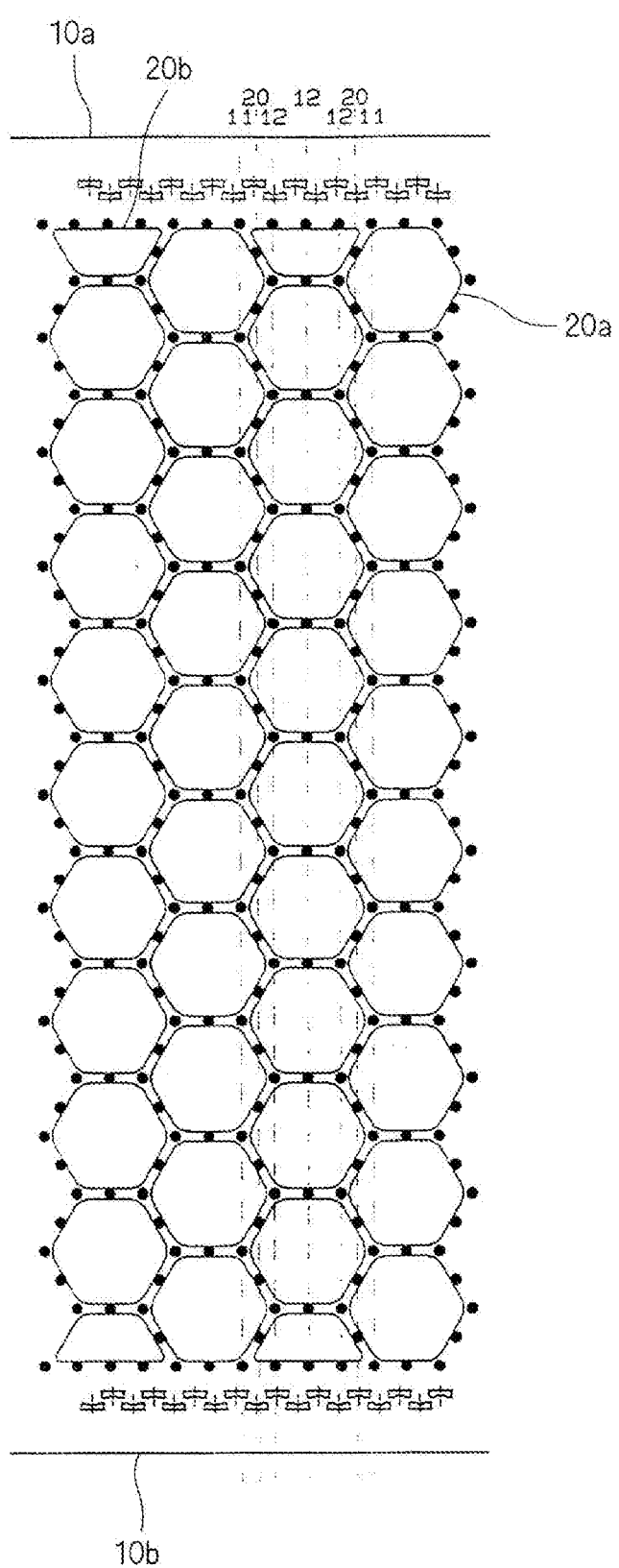
FIG. 5 is a main part plan view of an absorbent body (Modification 1).

FIG. 5 is a main part plan view of an absorbent body of Modification 1 of Embodiment 1. As shown in FIG. 5, the small regions 20a having a regular hexagonal shape encircled by the connections are arranged in the form of a honeycomb. Three connections are arranged in each side of the imaginary polygon corresponding to the small region 20a and then one of them is formed on a middle part of the side. The rows of the small regions 20a are arranged in a direction perpendicular to the long sides 10a and 10b. Thus, in the vicinity of the long sides 10a and 10b, the nonwoven fabric sheets are compartmentalized into the small regions 20b of trapezoidal shape encircled by the connections along these long sides 10a and 10b. In this small region 20b, five connections are arranged on the base side of the trapezoid serving as an imaginary polygon. Three of them are formed at a middle part of the side.

The connections are arranged in a plurality of rows parallel to a direction at right angles to the long sides 10a and 10b (in a direction parallel to the short sides). As for the number of connections per each of these rows, the minimum number is 11, the maximum number is 20, and hence the minimum number is 55% of the maximum number.

<Modification 2>

Figure 6:
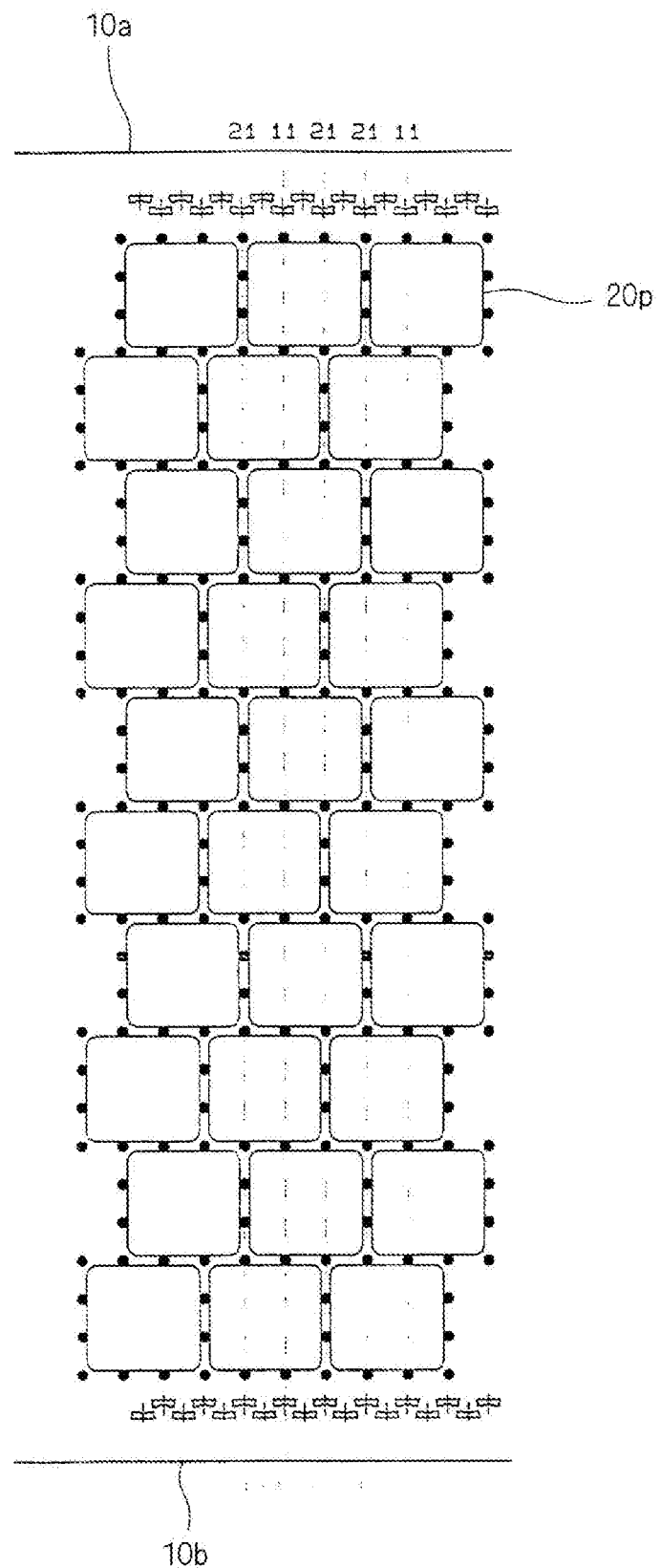
FIG. 6 is a main part plan view of an absorbent body (Modification 2).

FIG. 6 is a main part plan view of an absorbent body of Modification 2 of Embodiment 1. As shown in FIG. 6, the small regions 20p having a square shape encircled by the connections are alternately arranged with a deviation of approximately 1/3 pitch. Four connections are arranged in each side of the imaginary polygon corresponding to the small region 20p and then two of them are formed on a middle part of the side.

The connections are arranged in a plurality of rows parallel to a direction at right angles to the long sides 10a and 10b (in a direction parallel to the short sides). As for the number of connections per each of these rows, the minimum number is 11, the maximum number is 21, and hence the minimum number is 52% of the maximum number.

<Modification 3>

Figure 7:
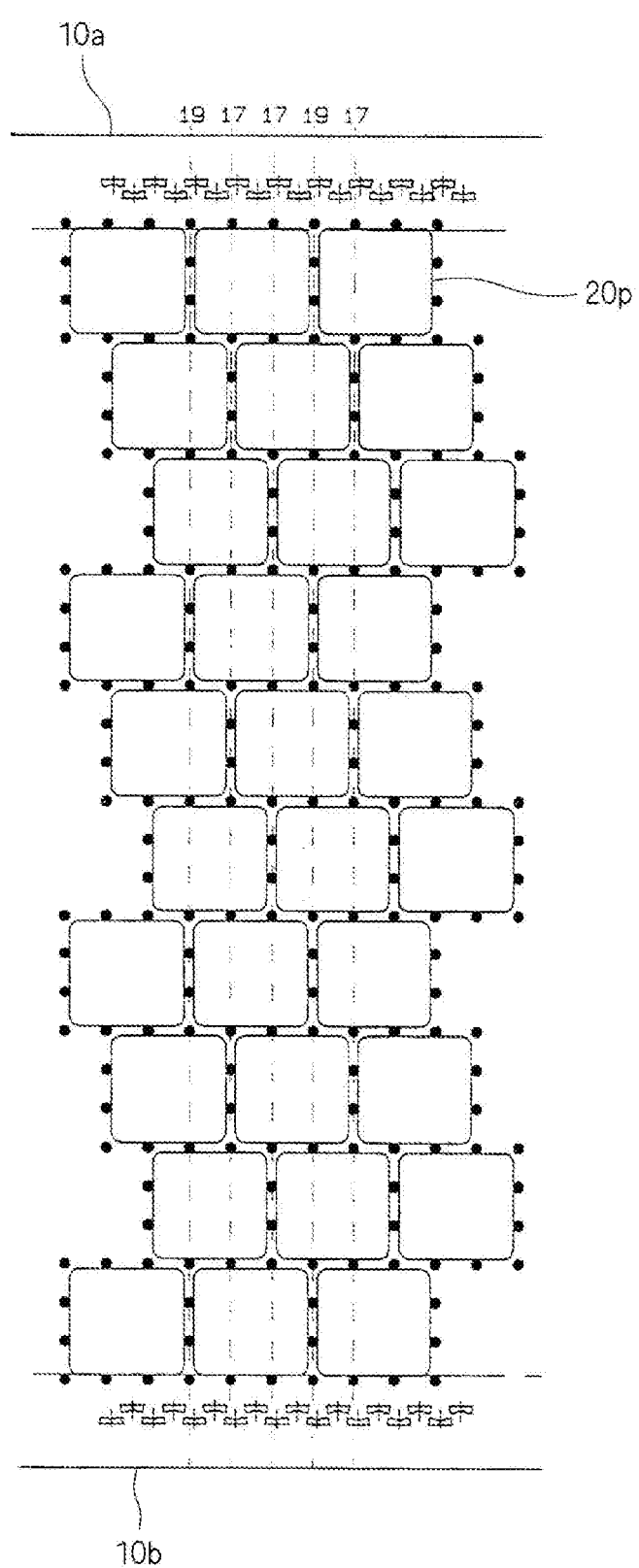
FIG. 7 is a main part plan view of an absorbent body (Modification 3).

FIG. 7 is a main part plan view of an absorbent body of Modification 3 of Embodiment 1. As shown in FIG. 7, the small regions 20$p$ having a square shape encircled by the connections are arranged between the long sides 10$a$ and 10$b$ with a deviation of ⅓ pitch or ⅔ pitch. Four connections are arranged in each side of the imaginary polygon corresponding to the small region 20$p$ and then two of them are formed on a middle part of the side.

The connections are arranged in a plurality of rows parallel to a direction at right angles to the long sides 10$a$ and 10$b$ (in a direction parallel to the short sides). As for the number of connections per each of these rows, the minimum number is 17, the maximum number is 19, and hence the minimum number is 89% of the maximum number.

<Modification 4>

Figure 8:
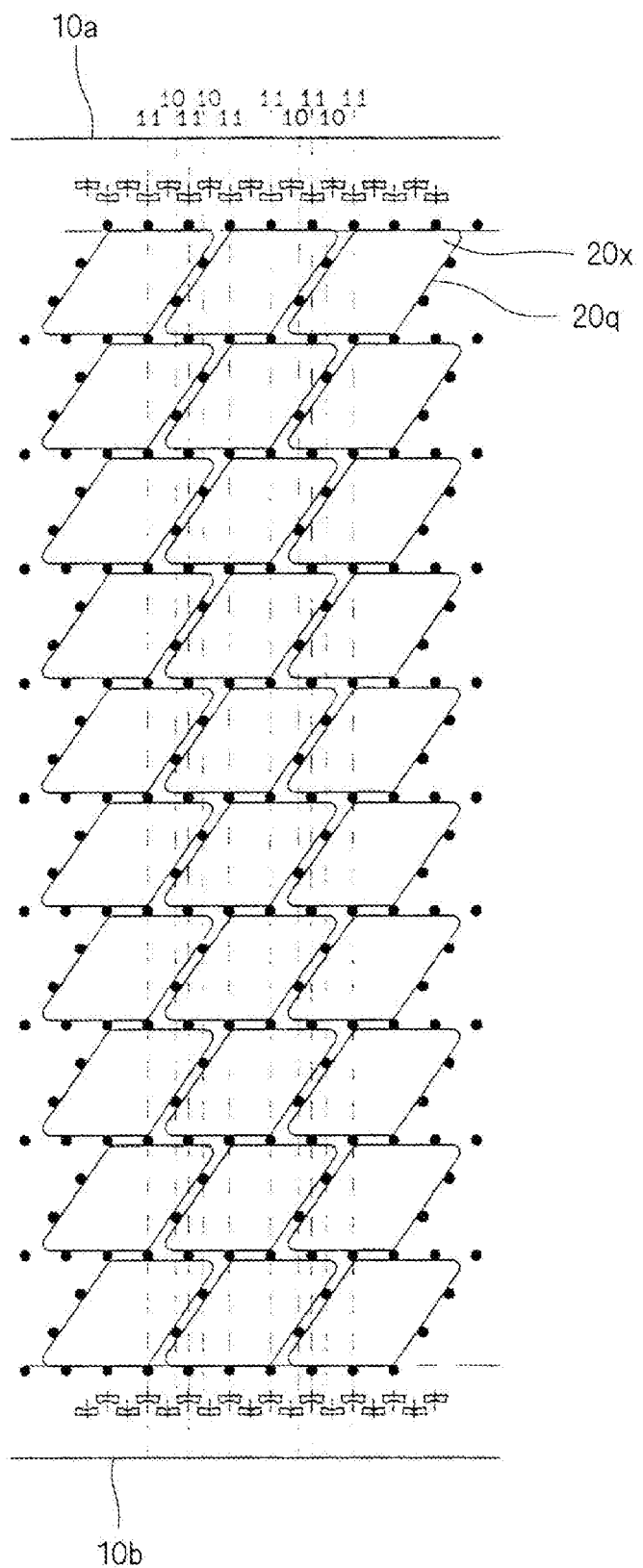
FIG. 8 is a main part plan view of an absorbent body (Modification 4).

FIG. 8 is a main part plan view of an absorbent body of Modification 4 of Embodiment 1. As shown in FIG. 8, the small regions 20$q$ having a rhombus shape encircled by the connections are arranged in the form of a lattice. Four connections are arranged on each side of the imaginary polygon corresponding to the small region 20$q$ and then two of them are formed on a middle part of the side.

The connections are arranged in a plurality of rows parallel to a direction at right angles to the long sides 10$a$ and 10$b$ (in a direction parallel to the short sides). As for the number of connections per each of these rows, the minimum number is 10, the maximum number is 11, and hence the minimum number is 91% of the maximum number.

<Modification 5>

Figure 9:
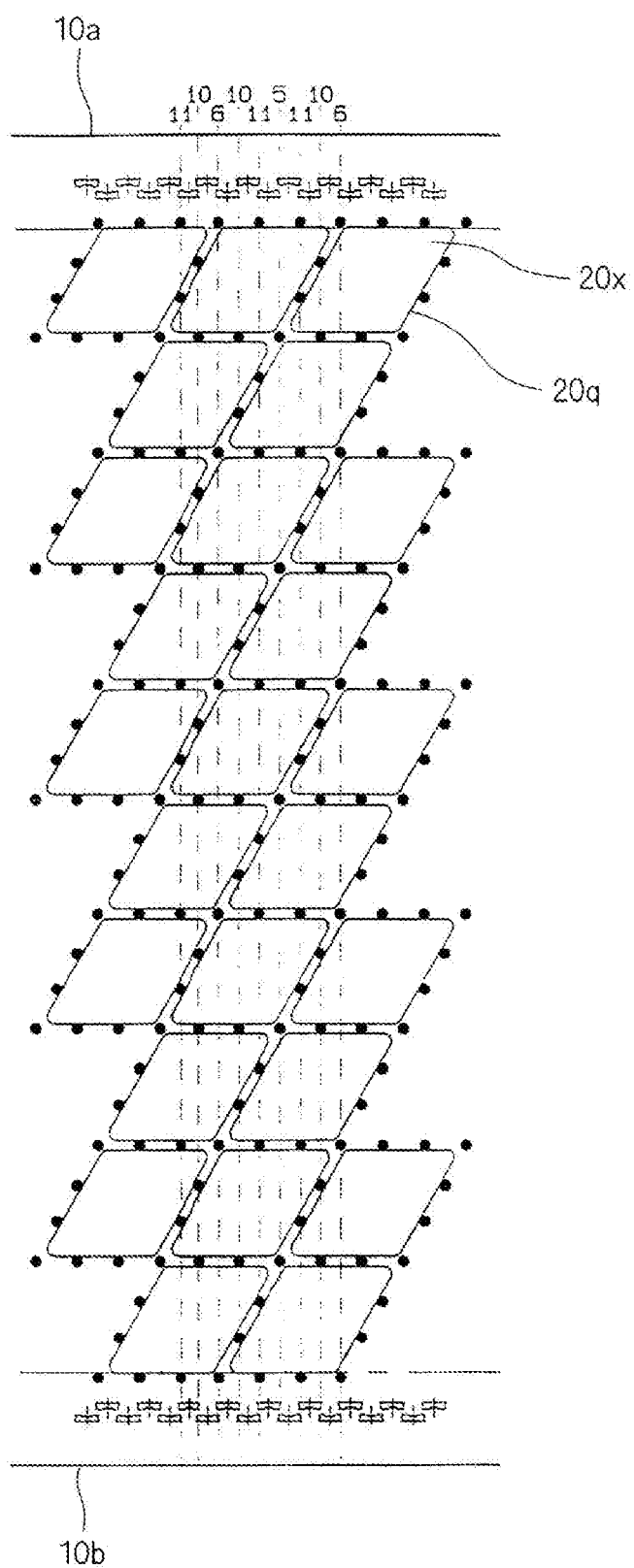
FIG. 9 is a main part plan view of an absorbent body (Modification 5).

FIG. 9 is a main part plan view of an absorbent body of Modification 5 of Embodiment 1. As shown in FIG. 9, the small regions 20$q$ having a rhombus shape encircled by the connections are alternately arranged with a deviated pitch. Four connections are arranged on each side of the imaginary polygon corresponding to the small region 20$q$ and then two of them are formed on a middle part of the side.

The connections are arranged in a plurality of rows parallel to a direction at right angles to the long sides 10$a$ and 10$b$ (in a direction parallel to the short sides). As for the number of connections per each of these rows, the minimum number is 5, the maximum number is 11, and hence the minimum number is 45% of the maximum number.

<Modification 6>

Figure 10:
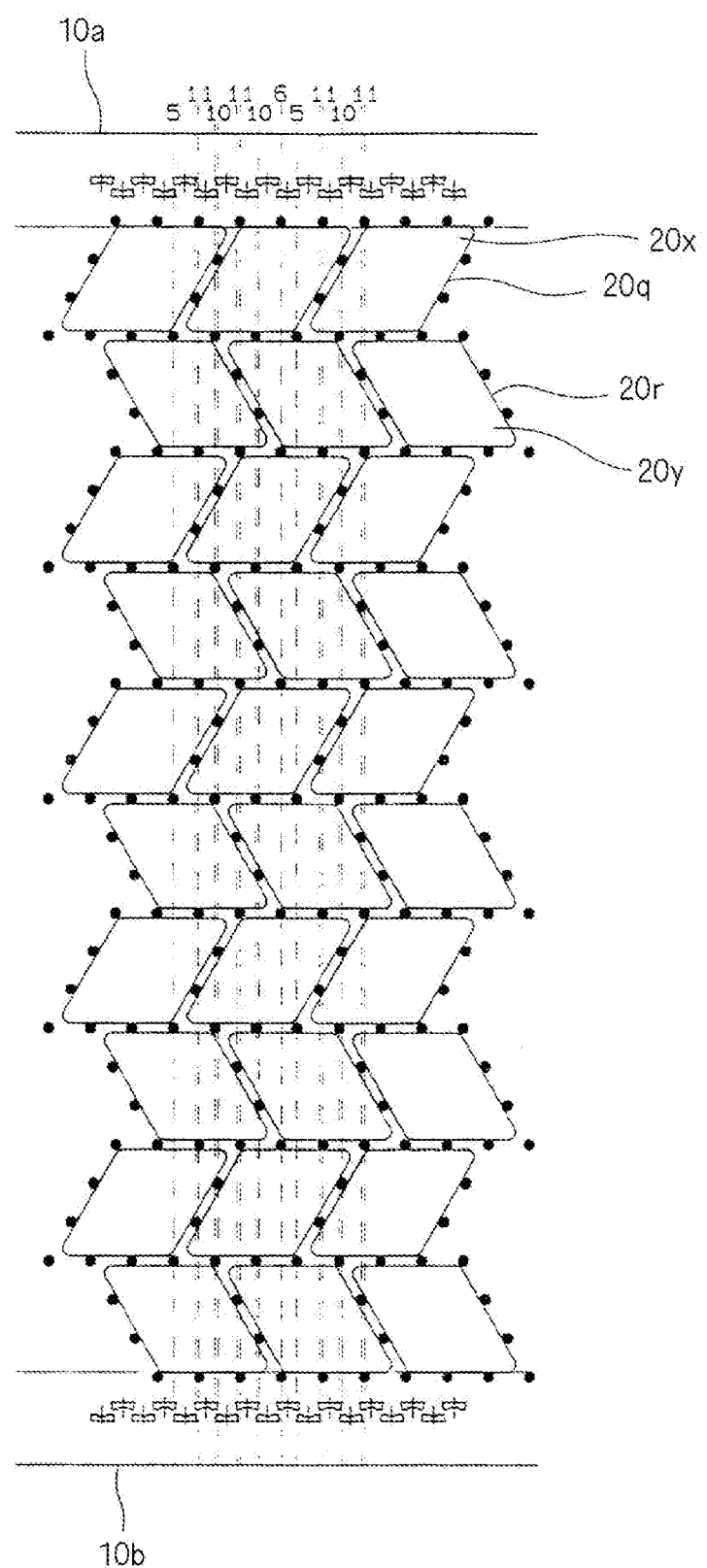
FIG. 10 is a main part plan view of an absorbent body (Modification 6).

FIG. 10 is a main part plan view of an absorbent body of Modification 6 of Embodiment 1. As shown in FIG. 10, the small regions 20$q$ and 20$r$ each having a rhombus shape encircled by the connections are alternately arranged in opposite orientation with a deviated pitch. Four connections are arranged on each side of the imaginary polygon corresponding to the small region 20$q$ or 20$r$ and then two of them are formed on a middle part of the side.

The connections are arranged in a plurality of rows parallel to a direction at right angles to the long sides 10$a$ and 10$b$ (in a direction parallel to the short sides). As for the number of connections per each of these rows, the minimum number is 5, the maximum number is 11, and hence the minimum number is 45% of the maximum number.

Also in Modifications 1 to 6 of Embodiment 1 given above, in a case that the absorbent body is produced such that in a state that the webs of the nonwoven fabric sheets are moved in a direction parallel to the long sides 10$a$ and 10$b$, the connections are formed simultaneously for each row arranged in a direction at right angles to the long sides 10$a$ and 10$b$ by ultrasonic jointing or heat sealing and, after that, the webs are cut out, even when variation in the magnitude of the pressure acting on each connection is caused in association with fluctuation in the number of connections formed simultaneously, the maximum of the pressure acting on the connection can be suppressed, for example, within a range of twice or the like of the minimum. As a result, feedback control at a high speed can stably be performed and hence the pressure acting on each connection can be made within an appropriate range so that satisfactory connections can be formed.

Accordingly, satisfactory connections can be formed in a state that the webs are conveyed at a high speed.

As seen from Embodiment 1 and Modifications 1 to 6 of Embodiment 1, as for the plurality of rows of the connections arranged in a direction at right angles to the long sides, when the minimum number of the connections per one row is equal to or greater than 45% of the maximum number of connections per one row, satisfactory connections can be formed in a state that the webs are conveyed at a high speed.

In Modifications 4 to 6, as shown in FIGS. 8 to 10, the acute portions 20$x$ and 20$y$ are formed in the small regions 20$q$ and 20$r$ having a rhombus shape encircled by the connections. It is difficult that the absorbent material is sufficiently disposed in the acute portions 20$x$ and 20$y$. Like in Embodiment 1 and Modifications 1 to 3, when all interior angles of the imaginary polygon are 90 degrees or larger, the absorbent material can easily be disposed even to the edges of the small region encircled by the connections. Thus, this configuration is preferable. Like in Embodiment 1, when all interior angles of the imaginary polygon are 120 degrees, the absorbent material can more easily be disposed even to the edges of the small region encircled by the connections. Thus, this configuration is more preferable.

Comparison Example 1

Figure 11:
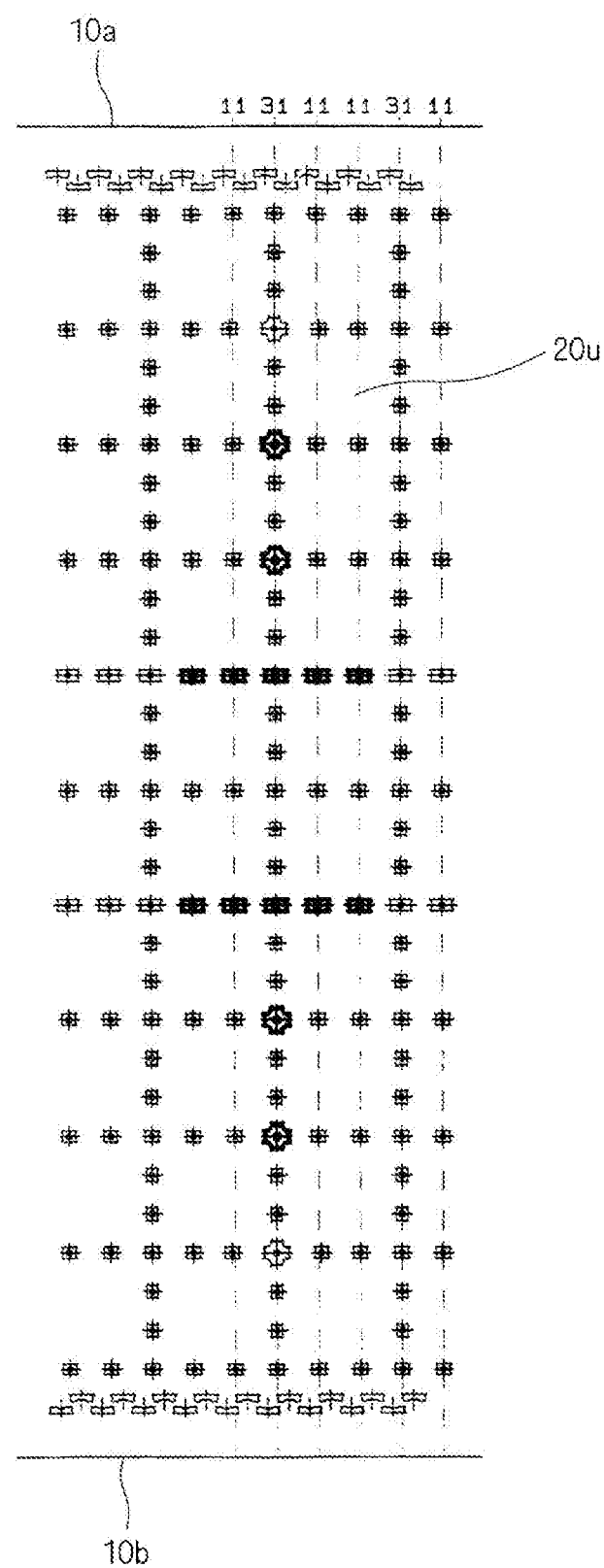
FIG. 11 is a main part plan view of an absorbent body (Comparison Example 1).

FIG. 11 is a main part plan view of an absorbent body of Comparison Example 1. As shown in FIG. 11, the small regions 20$u$ having a square shape encircled by the connections is arranged in the form of a lattice. Four connections are arranged in each side of the imaginary polygon corresponding to the small region 20$u$.

The connections are arranged in a plurality of rows parallel to a direction at right angles to the long sides 10$a$ and 10$b$ (in a direction parallel to the short sides). As for the number of connections per each of these rows, the minimum number is 11, the maximum number is 31, and hence the minimum number is 35% of the maximum number.

In Comparison Example 1, the difference in the magnitude of the pressure acting on each connection caused in association with fluctuation in the number of connections formed simultaneously becomes large. That is, the maximum of the pressure acting on the connection becomes 3 times or the like of the minimum. Thus, the feedback control of changing the magnitude of the force of pressing the ultrasonic horn or the heat sealing roll against the webs in accordance with the number of connections formed simultaneously, which is performed in order that the pressure acting on the connection may fall within an appropriate range, easily becomes unstable. Then, this feedback control becomes more unstable when the webs are conveyed at a high speed (e.g., a conveyance speed of 150 m/min or higher). Thus, formation of satisfactory connections becomes difficult when the webs are conveyed at a high speed.

Embodiment 2

In Embodiment 2, an absorbent body producing device 30 for producing the absorbent body 10 of Embodiment 1 is described below with reference to FIGS. 12 to 14.

Figure 12:
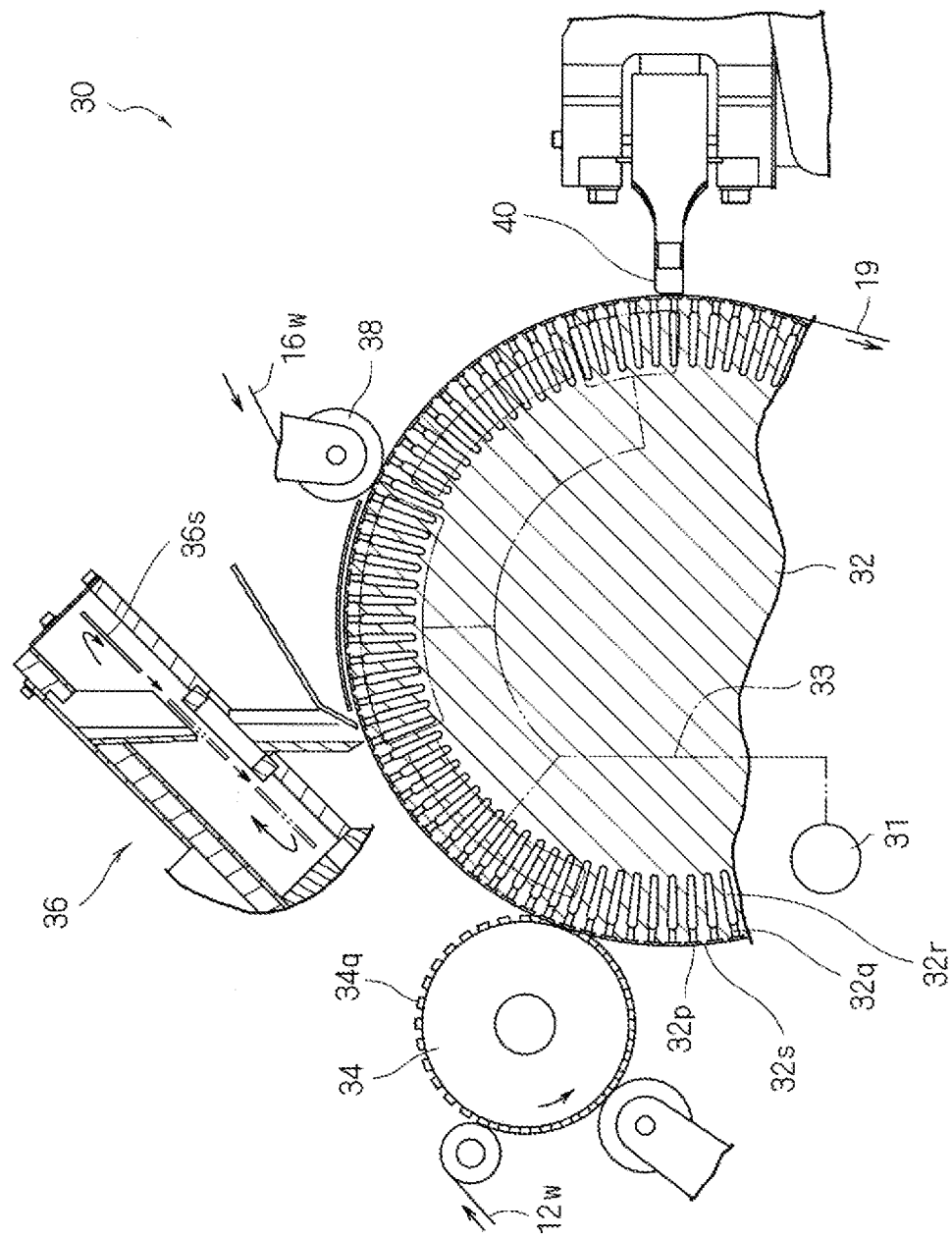
FIG. 12 is an explanation diagram of an absorbent body producing device (Embodiment 2).

FIG. 12 is an explanation diagram schematically showing the configuration of the absorbent body producing device 30. As shown in FIG. 12, in the absorbent body producing device 30, a shaping roll 34, an absorbent material supply unit 36, an introduction roll 38, an opposing member 40, and the like are arranged in the surroundings of the rotating roll 32.

Figure 13:
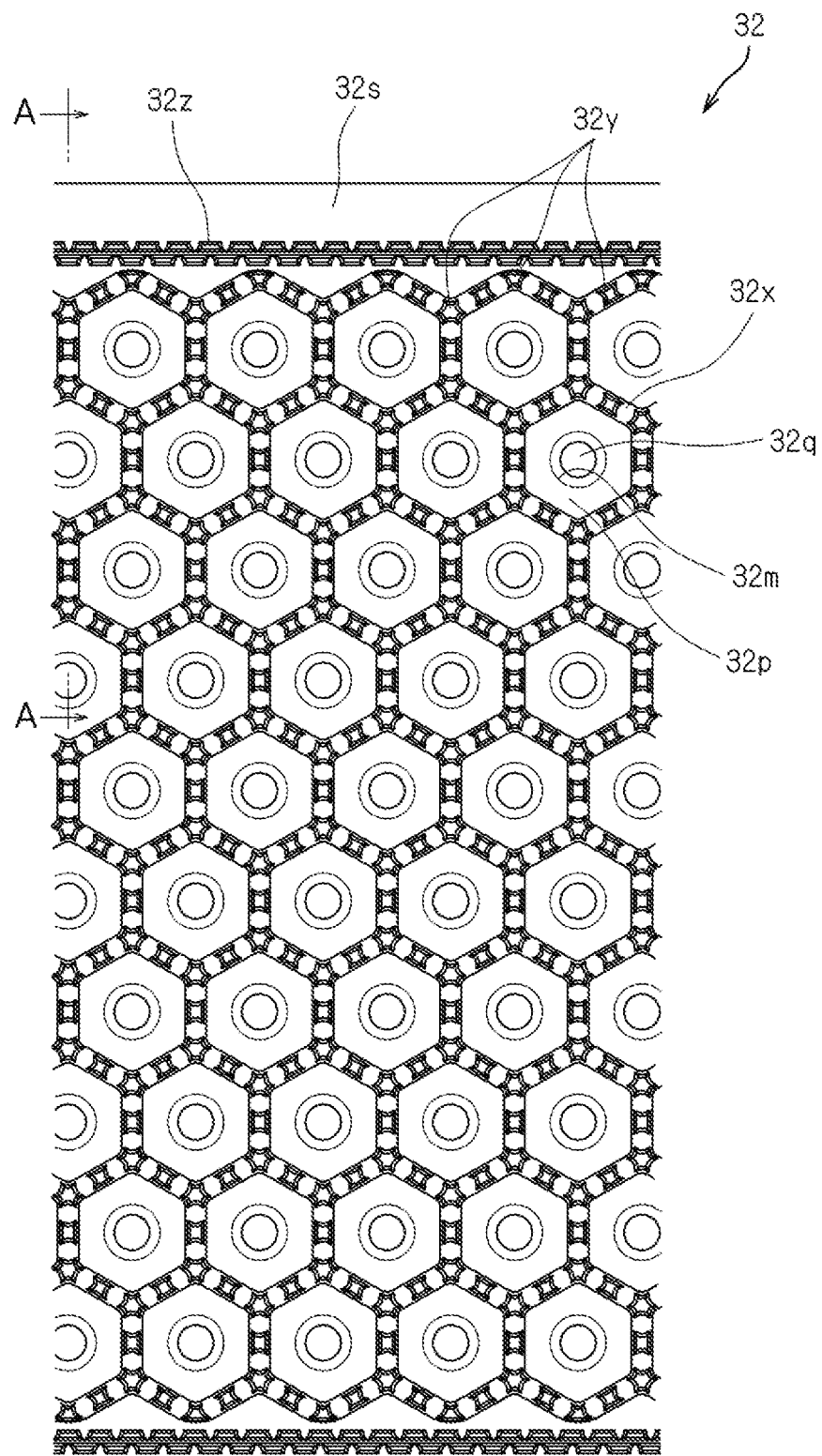
FIG. 13 is a development view of a rotating drum (Embodiment 2).
Figure 14:
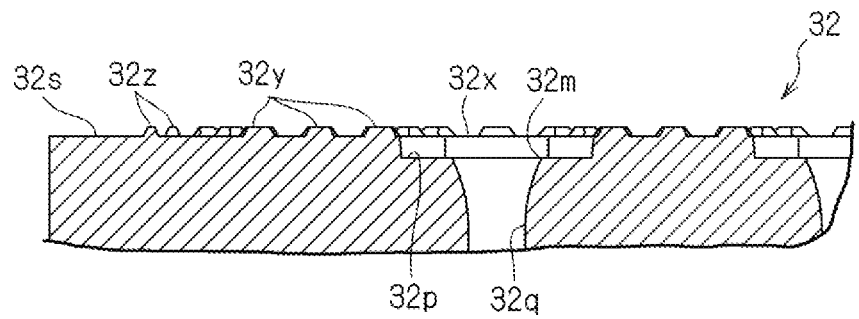
FIG. 14 is an enlarged sectional view taken along arrow line A-A in FIG. 13 (Embodiment 2).
Figure 15:
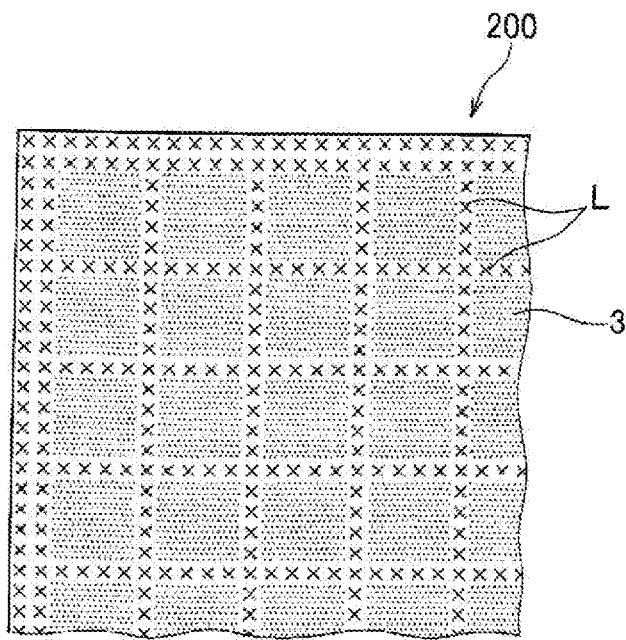
FIG. 15 is a main part plan view of an absorbent body (Conventional Example 1).
Figure 16:
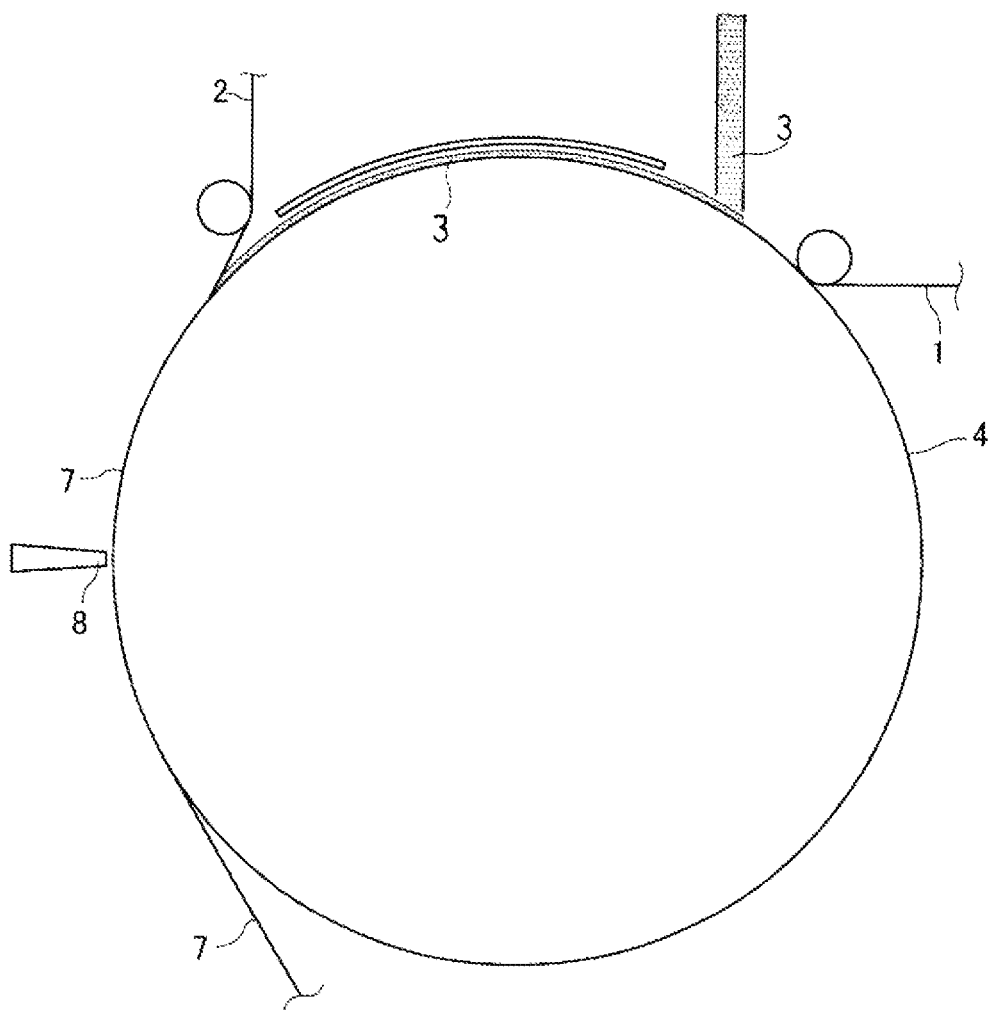
FIG. 16 is an explanation diagram of absorbent body producing device (Conventional Example 1).

FIG. 13 is a development view of the rotating roll 32. In FIG. 13, the up and down directions are directions parallel to the rotational center axis of the rotating roll 32. FIG. 14 is an enlarged sectional view taken along arrow line A-A in FIG. 13 and is an axial sectional view of the main part of the rotating roll 32. As shown in FIG. 13, the outer peripheral surface 32s of the rotating roll 32 includes a mesh-like portion 32x extending in a mesh-like shape. The mesh-like portion 32x includes the sides of the imaginary polygons located adjacent to each other so as to compartmentalize the outer peripheral surface of the rotating roll 32 and extends in a mesh-like shape along the sides of the imaginary polygons. As shown in FIGS. 13 and 14, in the mesh-like portion 32x, protrusions 32y are formed that protrude from the mesh-like portion 32x to the outside in a radial direction of the rotating roll 32. In the inner portion surrounded by the mesh-like portion 32x, a recess 32p is formed that retreats from the mesh-like portion 32x to the inner side in a radial direction of the rotating roll 32. In the bottom face of the recess 32p, an opening 32m in fluid communication with a suction hole 32q is formed.

By virtue of the protrusions 32y of the totaling roll 32, the connections 22, 23, and 24 are formed in the absorbent body 10 of Embodiment 1. A plurality of the protrusions 32y are formed with spaces therebetween in each side of the imaginary polygons located adjacent to each other so as to compartmentalize the outer peripheral surface 32s of the rotating roll 32. In the side common to the imaginary polygons adjacent to each other, the protrusions 32y are formed respectively on both ends and on a middle part except for both ends. The protrusions 32y form a plurality of rows parallel to the rotational center axis of the rotating roll 32 and then the minimum number of the protrusions 32y per one row is equal to or greater than 45% of the maximum number of the protrusions 32y per one row. It is preferable that at least three connections 32y are formed in each side of the imaginary polygon.

Within the outer peripheral surface 32s of the rotating roll 32, in the region where the protrusions 32y are formed, two rows of outer peripheral protrusions 32z are formed respectively on both sides in a direction parallel to the rotational center axis of the rotating roll 32. Here, three or more rows of the outer peripheral protrusions 32z may be formed. The outer peripheral protrusions 32z form rows at intervals in a circumferential direction of the outer peripheral surface 32s of the rotating roll 32 (in the right and left directions in FIG. 13) and the rows of the outer peripheral protrusions 32z are adjacent to each other in a direction parallel to the rotational center axis of the rotating roll 32 (in the up and down directions in FIG. 13). The outer peripheral protrusions 32z are alternately arranged for each row. When viewed in a direction parallel to the rotational center axis of the rotating roll 32, the outer peripheral protrusions 32z overlap with each other and are continuous respectively on each side in a direction parallel to the rotational center axis of the rotating roll 32.

As shown in FIG. 12, the recess 32p leads to the first suction hole 32q extending in a radial direction of the rotating roll 32 and then goes into fluid communication with a second suction hole 32r extending in parallel to the rotational center axis of the rotating roll 32. The suction hole 32r leads to a suction passage 33 arranged adjacent to the side surface of the rotating roll 32 and then leads to a vacuum pump 31. By virtue of this, the webs and the absorbent material can be suctioned to the outer peripheral surface 32s of the rotating roll 32.

The outer peripheral surface of the shaping roll 34 is provided with protrusions 34q fit into the recesses 32p of the rotating roll 32. The first web 12w is arranged along the protrusions 34q of the shaping roll 34. Then, the first web 12w is moved and conveyed together with the shaping roll 34 in accordance with rotation of the shaping roll 34, so as to be guided to the outer peripheral surface 32s of the rotating roll 32. The first web 12w may be composed of a single sheet of nonwoven fabric or, alternatively, composed of overlaid two or more sheets.

When guided to the outer peripheral surface 32s of the rotating roll 32, the first web 12w is pushed in the recesses 32p of the rotating roll 32 by the protrusions 34q of the shaping roll 34 so that the containing parts 14 (see FIG. 2) are formed.

The absorbent material supply unit 36 is arranged adjacent to the rotating roll 32 and opposite to the outer peripheral surface 32s of the rotating roll 32. The absorbent material supply unit 36 supplies the absorbent material to the containing parts 14 (see FIG. 2) formed in the first web 12w.

The introduction roll 38 guides the second web 16w and then overlay the second web 16w onto the first web 12w in which the absorbent material has been supplied to the containing parts 14 (see FIG. 2). The second web 16w may be composed of a single sheet of nonwoven fabric or, alternatively, composed of overlaid two or more sheets.

The opposing member 40 is arranged adjacent to the rotating roll 32, then extends in parallel to the rotational center axis of the rotating roll 32, and then opposes the outer peripheral surface 32s of the rotating roll 32. The opposing member 40 is an ultrasonic horn for providing ultrasonic vibration. In place of this, a member such as a heat sealing roll for supplying heat may be employed. Here, when the opposing member 40 is a member for supplying heat, a configuration may be employed that heat is supplied also from the rotating roll 32 when necessary. The opposing member 40 presses the portion where the second web 16w is overlaid on the first web 12w, against the protrusions 32x and 32y of the outer peripheral surface 32s of the rotating roll 32 (see FIGS. 13 and 14) and then, in this state, transmits ultrasonic vibration or heat to the webs 12w and 16w so as to form the connections where the first and the second web 12w and 16w are connected together. The connections where the first and the second web 12w and 16w are connected together is formed in correspondence to the protrusions formed in the outer peripheral surface 32s of the rotating roll 32.

In this case, even when the magnitude of the pressure acting on each connection varies in association with fluctuation of the number of connections formed simultaneously, that is, fluctuation of the number of protrusions contained in a row parallel to the rotational center axis of the rotating roll 32, the maximum of the pressure acting on the connection can be suppressed, for example, within a range of twice or the like of the minimum. Thus, feedback control at a high speed can stably be performed and the pressure acting on each protrusion can be made within an appropriate range. As a result, satisfactory connections can be formed in a state that the webs are conveyed at a high speed.

The employed shape of the imaginary polygons for compartmentalizing the outer peripheral surface 32s of the rotating roll 32 is not limited to a regular hexagon and may suitably be selected. When all interior angles of the imaginary polygon are 90 degrees or larger, the absorbent material can easily be disposed even to the edges of the small region encircled by the connections and hence this configuration is preferable. When the angles are 120 degrees, the absorbent material can more easily be disposed even to the edges of the small region encircled by the connections and hence this configuration is more preferable.

The first and the second web 12w and 16w connected together by the absorbent body producing device are cut out by a cutting device (not shown) so that individual pieces of the absorbent body are separated from each other.

In a case that supply of the absorbent material by the absorbent material supply unit 36 is suspended in correspondence to the cut position of the first and the second web 12w and 16w connected together, the first and the second web 12w and 16w connected together can stably be cut out.

For example, the absorbent material supply unit 36 supplies the absorbent material to the first web 12w in a state that supply of the absorbent material is suspended with a fixed period for a portion facing at least four rows of imaginary polygons arranged in a direction parallel to the rotational center axis of the rotating roll 32 within the first web 12w. In this case, supply of the absorbent material is suspended with a fixed period for the portion facing at least four rows of imaginary polygons arranged in a direction parallel to the rotational center axis of the rotating roll 32. When the webs are cut at the center of the portion where the absorbent material is not disposed, as shown in FIG. 1, the absorbent body 10 can successively be produced in which the absorbent material is not disposed in at least two adjacent rows of the small regions in the end region.

<Summary>

As described above, in the absorbent body of Embodiment 1 and Modifications 1 to 6 of Embodiment 1 and the absorbent body producing device of Embodiment 2, satisfactory connections can be formed in a state that the webs are conveyed at a high speed. In particular, when the connections are formed by connecting together the webs by ultrasonic jointing, satisfactory connections can be formed.

In addition, the present invention is not limited to the above-described embodiments, and various modifications may be applied to implement the invention.

For example, connections may be formed in which another member, such as a water-permeable mesh sheet, a non-water-permeable film, or the like, is arranged on one side or both sides of the absorbent body or between the nonwoven fabric sheets, and then the nonwoven fabric sheets are directly connected together with the another member, or the nonwoven fabric sheets are connected through another member in between.

DESCRIPTION OF REFERENCE NUMERALS

10 Absorbent body
10a, 10b Long side
10c, 10d Short side
11 Middle region
11p, 11q End region
12 Nonwoven fabric sheet
12w First web
14 Containing part
16 Nonwoven fabric sheet
16w Second web
18 Absorbent material
20, 20a, 20p to 20u Small region
20x, 20y Acute portion
21 Imaginary polygon
22 Connection
22x Acute portion
23 Connection
23x, 23y Acute portion
24 Connection
24x Acute portion
26, 28 Outer peripheral connection
30 Absorbent body producing device
32 Rotating roll
32p Recess
32s Outer peripheral surface
32x Mesh-like portion
32y Protrusion
32z Outer peripheral protrusion
36 Absorbent material supply unit
40 Opposing member

The invention claimed is:

1. An absorbent body comprising:
at least two nonwoven fabric sheets overlaid with each other and having a first pair of sides parallel to each other;
connections for connecting together the nonwoven fabric sheets so as to cause the nonwoven fabric sheets to contact with each other at the connections; and
an absorbent material that is disposed in a first region encircled by the connections between the nonwoven fabric sheets, wherein
as for the connections, when viewed in a direction perpendicular to a main surface of the nonwoven fabric sheets, a plurality of the connections is formed with spaces therebetween on each of sides of imaginary polygons that compartmentalize the nonwoven fabric sheets and that are adjacent to each other,
among the connections, the imaginary polygons include only the connections arranged on the sides of the imaginary polygons,
the connections are arranged at least on a middle part of a side common to the imaginary polygons adjacent to each other,
the connections are arranged in a plurality of rows parallel to a direction at right angles to the first pair of sides,
the plurality of rows of the connections is parallel to each other, and
a minimum number of the connections per one of the plurality of rows is equal to or greater than 45% of a maximum number of the connections per one of the plurality of rows.

2. The absorbent body according to claim 1, wherein all interior angles of the imaginary polygons are 90 degrees or larger.

3. The absorbent body according to claim 1, wherein when viewed in a direction perpendicular to the main surface of the nonwoven fabric sheets, each of the connections has an acute portion protruding parallel to or substantially parallel to a direction in which the sides of the imaginary polygons extend.

4. The absorbent body according to claim 1, further comprising a pair of end regions, and a middle region which contains the first region, between the pair of end regions,
wherein each of the pair of end regions contains a plurality of second regions encircled by the connections, adjacent to an outer periphery of the nonwoven fabric sheets on each of one side and another side of the nonwoven fabric sheets in a direction at right angles to the plurality of rows of the connections, and the absorbent material is not disposed in at least two rows of the second regions contained in the pair of end regions, or an amount of the absorbent material disposed in the at least two rows of the second region contained in the pair of end regions is substantially smaller than an amount of the absorbent material disposed in the first region contained in the middle region.

5. The absorbent body according to claim 1, wherein:

a shape of the nonwoven fabric sheets is a rectangle having the first pair of sides and a second pair of sides; and the connections are arranged in the plurality of rows parallel to the second pair of sides.

6. The absorbent body according to claim 1, further comprising plural rows of outer peripheral connections which, when viewed in the direction perpendicular to the main surface of the nonwoven fabric sheets, are arranged with spaces therebetween in a vicinity of an outer periphery of the nonwoven fabric sheets along the outer periphery of the nonwoven fabric sheets and which are adjacent to each other in a direction perpendicular to the outer periphery of the nonwoven fabric sheets, wherein when viewed in a direction perpendicular to the outer periphery of the nonwoven fabric sheets and parallel to the main surface of the nonwoven fabric sheets, the outer peripheral connections in adjacent two rows of the plural rows overlap with each other as if the adjacent two rows of the outer peripheral connections were continuous.

7. The absorbent body according to claim 1, wherein the connections arranged on each of the sides of the imaginary polygons include a first side connection, a second side connection and a middle part connection between the first side connection and the second side connection, and each of the first side connection and the second side connection includes two acute portions protruding toward the middle part connection along each of the sides of the imaginary polygons and the middle part connection includes another two acute portions at each side of the middle part connection, protruding toward each of the first side connection and the second side connection along each of the sides of the imaginary polygons, to hold the absorbent material in the first region encircled with the connections arranged on each of the imaginary polygons.

8. The absorbent body according to claim 7, wherein each of the first side connection and the second side connection includes a curved portion between the two acute portions, and the middle part connection includes another curved portion between the another two acute portions at each side of the middle part connection facing the curved portion of each of the first side connection and the second side connection.

9. The absorbent body according to claim 1, wherein the at least two nonwoven fabric sheets include a first sheet and a second sheet connected to the first sheet through the connections, to form enclosed spaces between the first sheet and the second sheet as the first regions, and the absorbent material is stored in each of the enclose spaces.

\* \* \* \* \*